United States Patent
Hazin

(10) Patent No.: US 7,009,075 B2
(45) Date of Patent: Mar. 7, 2006

(54) PROCESS FOR THE SELECTIVE CONVERSION OF ALKANES TO UNSATURATED CARBOXYLIC ACIDS

(75) Inventor: Paulette N. Hazin, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 47 days.

(21) Appl. No.: 10/881,815

(22) Filed: Jun. 30, 2004

(65) Prior Publication Data

US 2006/0004228 A1   Jan. 5, 2006

(51) Int. Cl.
*C07C 51/16* (2006.01)

(52) U.S. Cl. .................. 562/549; 562/598; 502/311

(58) Field of Classification Search .............. None
See application file for complete search history.

(56) References Cited

U.S. PATENT DOCUMENTS

| | | | |
|---|---|---|---|
| 5,231,214 A | 7/1993 | Ushikubo et al. | |
| 5,281,745 A | 1/1994 | Ushikubo et al. | |
| 5,380,933 A | 1/1995 | Ushikubo et al. | |
| 5,994,580 A | 11/1999 | Takahashi et al. | |
| 6,063,728 A | 5/2000 | Hinago et al. | |
| 6,166,241 A * | 12/2000 | Kayou et al. | 558/318 |
| 6,746,983 B1 | 6/2004 | Gaffney et al. | |

FOREIGN PATENT DOCUMENTS

| | | |
|---|---|---|
| JP | 10045664 | 2/1998 |
| JP | 10057813 | 3/1998 |

* cited by examiner

*Primary Examiner*—Johann Richter
*Assistant Examiner*—Karl Puttlitz
(74) *Attorney, Agent, or Firm*—Jim Wheelington

(57) ABSTRACT

The invention disclosed is a process for the selective conversion of an alkane to an unsaturated carboxylic acid in a one-step process with a mixed metal oxide catalyst composition having the general formula:

$$MoV_aNb_bTe_cSb_dM_eO_x$$

wherein M is optional and may be one or more selected from silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum. This catalyst may be prepared by co-precipitation of metal compounds which are calcined to form a mixed metal oxide catalyst.

28 Claims, No Drawings

PROCESS FOR THE SELECTIVE CONVERSION OF ALKANES TO UNSATURATED CARBOXYLIC ACIDS

BACKGROUND OF THE INVENTION

1. Field of the Invention

This invention relates to a method for producing an unsaturated carboxylic acid from an alkane using a mixed metal oxide catalyst. In particular, this invention relates to a process for producing acrylic acid from propane by a single step vapor phase oxidation reaction with a mixed molybdovanadate catalyst containing tellurium and antimony.

2. Description of the Prior Art

The commercial production of an unsaturated carboxylic acid, such as acrylic acid or methacrylic acid, is by a catalytic reaction of an olefin, such as propylene or isobutylene, with oxygen to form an alkenylaldehyde, such as acrolein or methacrolein, which is subsequently catalytically reacted with oxygen. Alkanes, such as propane, have advantages of cost and of availability over olefins. Furthermore, a one step process would have advantages over the present commercial process.

There are examples of producing acrylic acid and other unsaturated carboxylic acids from propane and other alkanes in a one step vapor phase catalytic oxidation reaction. U.S. Pat. No. 5,380,933 discloses a catalyst of oxides of molybdenum, vanadium, tellurium, and elements selected from niobium, tantalum, tungsten, titanium, aluminum, zirconium, chromium, manganese, iron, ruthenium, cobalt, rhodium, nickel, palladium, platinum, antimony, bismuth, boron, indium or cerium.

U.S. Pat. No. 5,994,580 discloses a process for producing acrylic acid from propane and oxygen using a catalyst containing molybdenum, vanadium, antimony and at least one of niobium, tantalum, tin, tungsten, titanium, nickel, iron, chromium or cobalt.

Japanese published patent application H10-57813 discloses a metal oxide catalyst of molybdenum, vanadium, tellurium and/or antimony and an element selected from niobium, tantalum, tungsten, titanium, aluminum, zirconium, chromium, manganese, iron, ruthenium, cobalt, rhodium, nickel, palladium, platinum, bismuth, boron, indium, phosphorus, rare earth elements, alkali metals, alkali-earth metals.

Japanese published patent application H10-45664 discloses a catalyst of oxides of molybdenum, vanadium, antimony and an element selected from niobium, tantalum, tungsten, titanium, zirconium, chromium, iron, manganese, ruthenium, cobalt, rhodium, nickel, palladium, platinum, boron, indium, alkali metals, alkali-earth metals, and rare earth elements.

U.S. Pat. No. 6,746,983 discloses a catalyst to produce unsaturated carboxylic acids by vapor phase oxidation of an alkane or mixture of an alkane and an alkene. The catalyst is a mixed metal oxide of molybdenum, vanadium, one of tellurium, antimony or niobium, one of scandium, yttrium, lanthanum, rhenium, iridium, copper, silver, gold, zinc, gallium, silicon, germanium, arsenic, lead, sulfur, selenium, tin, bismuth, fluorine, chlorine, bromine or iodine. There is no disclosure of a molybdovanadate catalyst containing tellurium, antimony and niobium.

Catalyst with similar compositions have been used for processes other than those for producing acrylic acid and other unsaturated carboxylic acids from propane and other alkanes in a one step vapor phase catalytic oxidation reaction.

U.S. Pat. No. 5,231,214 discloses a process for producing a nitrile from an alkane and ammonia in the presence of a catalyst containing molybdenum, vanadium tellurium, niobium and at least one of magnesium, calcium, strontium, barium, aluminum, gallium, thallium, indium, titanium, zirconium, hafnium, tantalum, chromium, manganese, tungsten, iron, ruthenium, cobalt, rhodium, nickel, palladium, zinc, tin, lead, arsenic, antimony, bismuth, lanthanum or cerium. One example (Example 12) disclosed a catalyst of the composition $MoV_{0.4}Te_{0.2}Sb_{0.1}O_n$.

U.S. Pat. No. 5,281,745 discloses a process for producing a nitrile from an alkane and ammonia in the presence of a catalyst containing molybdenum, vanadium, tellurium and at least one of niobium, tantalum, tungsten, titanium, aluminum, zirconium, chromium, manganese, iron, ruthenium, cobalt, rhodium, nickel, palladium, platinum, antimony, bismuth, boron or cerium and having a particular X-ray diffraction pattern. One example (Example 4) and a comparative example (Comparative Example 4) disclosed a catalyst of the composition $MoV_{0.4}Te_{0.2}Sb_{0.1}O_n$.

U.S. Pat. No. 6,063,728 discloses an ammoxidation catalyst of molybdenum, vanadium, niobium, at least one of tellurium and antimony and optionally at least one of tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead and phosphorus and of a particular X-ray diffraction pattern.

Tellurium can become volatile at the temperatures used for the oxidation of propane to acrylic acid (350–425° C.). Catalyst performance can be affected by the loss of tellurium. In addition, tellurium is an environmental hazard which must be contained or controlled with means which add to the overall process costs.

SUMMARY OF THE INVENTION

This invention is a process for producing an unsaturated carboxylic acid, such as acrylic acid or methacrylic acid, from an alkane, such as propane or isobutane, with a mixed metal oxide catalyst. The catalyst has a composition of $MoV_aNb_bTe_cSb_dM_eO_x$ wherein optional element M is one or more elements from silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum; a is 0.05 to 0.99, preferably 0.1 to 0.5, most preferably 0.3; b is 0.01 to 0.99, preferably 0.05 to 0.2, most preferably 0.05 to 0.12; c is 0.01 to 0.15, preferably 0.01 to 0.12, most preferably 0.01 to 0.10; d is 0.01 to 0.2, preferably 0.01 to 0.15, most preferably 0.03 to 0.1; e is 0 to 0.5, preferably 0.01 to 0.25, most preferably 0.02 to 0.1; and x is determined by the valence requirements of the other components of the catalyst composition.

DESCRIPTION OF EMBODIMENTS OF THE INVENTION

This invention is generally a mixed metal oxide catalyst and, more specifically, a molybdovanate catalyst. The catalyst of the present invention is a mixture of oxides of molybdenum, vanadium, niobium, tellurium and antimony. In addition, it may contain oxides of other metals, such as silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum. The present catalyst contains a reduced amount of tellurium. A lesser amount of tellurium may be used in the catalyst if antimony is present.

The catalyst of the present invention has the composition described in the following formula:

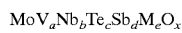

$$MoV_aNb_bTe_cSb_dM_eO_x$$

wherein optional element M may be one or more selected from silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium or lanthanum; a is 0.05 to 0.99, preferably 0.1 to 0.5, most preferably 0.3; b is 0.01 to 0.99, preferably 0.05 to 0.2, most preferably 0.05 to 0.12; c is 0.01 to 0.15, preferably 0.01 to 0.12, most preferably 0.01 to 0.10; d is 0.01 to 0.2, preferably 0.01 to 0.15, most preferably 0.03 to 0.1; e is 0 to 0.5, preferably 0.01 to 0.25, most preferably 0.02 to 0.1; and x is determined by the valence requirements of the other components of the catalyst composition.

This catalyst may be used in a one-step process for producing an unsaturated carboxylic acid, such as acrylic acid or methacrylic acid, from an alkane, such as propane or isobutane. The alkane is preferably one having three to eight carbon atoms and is most preferable propane or isobutane. The process is preferably a vapor phase reaction in which the catalyst in brought into contact with an alkane and oxygen. The molar ratio of alkane:oxygen is preferably in the range of from 0.05:1 to 10:1. The contact time for the reactants preferably is in the range of from 0.1 to 10 seconds, preferably 0.1 to 5 seconds. Steam may be added to the reaction gases. If steam is used, the molar ratio of alkane:steam is in the range from 0.05:1 to 10:1. In addition, an inert gas such as nitrogen, argon or helium may be used a carrier medium. If a carrier medium is used, the molar ratio of alkane:carrier preferably is in the range from 0.1:1 to 10:1.

The reaction temperature for the method of using the present invention is 320–450° C., preferably 350–400° C. The reaction pressure is 0 to 75 psig, preferably 5 to 50 psig.

The method of using the present invention will, in addition to the unsaturated carboxylic acid, produce byproducts, including an olefin. For example, when the alkane is propane, byproducts of carbon monoxide, carbon dioxide, acetic acid and propylene will be formed. The olefin, such as propylene, may be separated from the other byproducts and recycled into the feed stream. The catalyst and process of the present invention can convert an olefin into an unsaturated carboxylic acid, e.g., propylene into acrylic acid. In the alternative, the olefin may be separated from the other byproducts and converted to an unsaturated carboxylic acid in a separate process using known catalysts for converting an olefin into an unsaturated carboxylic acid or used in other processes to produce other products.

The catalyst of the present invention may be used as an unsupported catalyst or a supported catalyst. If supported, the support should be an inert solid which is chemically unreactive with any of the active components of the catalyst and is preferably silica, alumina, niobia, titania, zirconia or mixtures thereof. The catalyst may be affixed to the support by methods known in the art, including incipient wetness, slurried reactions and spray drying. The catalyst is not limited by shape, size or particle distribution and may be formed as appropriate for the reaction vessel in the process. Examples are powder, granules, spheres, cylinders, saddles, etc.

Preferably, the catalyst is prepared from a solution of water-soluble compounds of each of the component metals. If the compounds are insoluble in water, a slurry or suspension may be formed and thoroughly dispersed or mixed. In the alternative, a solvent other than water, such as an acid or an alkali, may be used. Heat may be applied to facilitate dissolution in the solvent. Generally, a mixture of compounds of the elements, such as salts of other complexes, in the approximate desired gram-atom ratio is dissolved to form a solution. The liquid solvent is removed and the resulting catalyst composition is dried and then calcined.

Suitable precursor molybdenum compounds are molybdenum salts, such as ammonium paramolybdate, molybdenum oxides, molybdic acids or molybdenum chlorides. Suitable precursor vanadium compounds are vanadium salts, such as ammonium metavanadate, vanadium oxides, vanadium oxalates or vanadium sulfates.

Suitable precursor niobium compounds are niobium oxalate, ammonium niobium oxalate, niobium oxide, hydrous niobium oxide or niobic acid. Oxalic acid and niobic acid may be dissolved in water to obtain a solution. With respect to the obtained solution, it is preferred that the molar ratio of oxalic acid to niobium is in the range of from 1:1 to 12:1, preferably from 3:1 to 6:1. A dicarboxylic acid other than oxalic acid, such as malonic acid, succinic acid, glutaric acid and adipic acid, or a tricarboxylic acid, such as citric acid, may be used with or without niobic acid to form a solution.

Suitable precursor tellurium compounds are telluric acid, tellurium dioxide and tellurium chloride.

Suitable precursor antimony compounds are antimony oxide, antimony chloride, antimony acetate, antimony tartrate and antimony sulfate.

Suitable precursor compounds of other metals, such as silver, silicon, sulfur, zirconium, titanium, aluminum, copper, lithium, sodium, potassium, rubidium, cesium, gallium, iron, rhenium, cobalt, chromium, manganese, indium, thallium, bismuth, germanium, tin, cerium or lanthanum, are salts such as oxalates, tartrates, citrates, nitrates, halides, carbonates, bicarbonates, hydroxides, oxides and the like with nitrate and oxalate salts being preferred. For phosphorus and arsenic, appropriate precursor compounds would include ammonium hydrogen phosphate, ammonium phosphate, phosphorus pentoxide, phosphoric acid, phosphorus acid, arsenic acid and arsenic oxide.

The liquid solvent may be removed by filtration, evaporation or centrifuge. If heat is used during removal of the liquid, preferably the temperature will be in the range from 40 to 100° C. Drying the catalyst composition is by methods known in the art. Spray drying may be used as a means to remove the liquid solvent and dry the catalyst in a single operation. After the catalyst composition is dried, preferably it is heat treated in air at a temperature in the range of 250–350° C. for 1 to 10 hours. Calcination of the catalyst composition preferably occurs in an inert gas, such as argon or nitrogen, at a temperature in the range of 550–650° C. for 1 to 10 hours.

The solid catalyst may be further prepared by high-energy ballmilling with a planetary ballmill or lower energy grinding or crushing means to obtain desired crystallite size, particle size, particle shape and/or particle size distribution.

There are two factors which contribute to a catalyst being useful for oxidation of an alkane to an unsaturated carboxylic acid. The first factor is the degree to which the alkane is converted (% conversion). The second is the extent to which the desired product is obtained (% selectivity). The product of these two factors in turn determine the overall yield of the catalyst in the oxidation of an alkane to an unsaturated carboxylic acid. The catalyst of the catalyst of the present invention can attain a conversion of propane of 80% and a selectivity to acrylic acid of 52% for an overall yield of 42%.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

A mixed metal oxide with a nominal composition of $Mo_1V_{0.3}Nb_{0.05}Sb_{0.15}T_{0.06}O_x$ was prepared as follows:

Solution A: Ammonium vanadate (7.95 g) was dissolved in 165 mL water at 90° C. The solution was purged with nitrogen. Antimony (III) oxide (4.92 g) was added and the mixture was heated at 91° C. for about 4 hrs. Heating was discontinued and the mixture was cooled in ice to 19° C. Ammonium paramolybdate (40.0 g) was added and the mixture was stirred overnight under nitrogen purge.

Solution B: Niobium oxalate mono oxalate (7.12 g) was stirred in 40 mL water overnight.

Solution C: Telluric acid (3.12 g) was dissolved in 40 mL water with heating.

Solution C was cooled to room temperature. Solution B was added to solution A followed by solution C and the resulting mixture was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground, pressed and sieved to 18/35 mesh. 2.7 g of this catalyst was tested for propane oxidation with a feed having a propane/O2/N2/water ratio of 1/2/18/15.3. The results are shown in table 1.

EXAMPLE 2

2.7 g of the catalyst prepared in example 1 was tested for propane oxidation with a feed having a propane/O2/N2/water ratio of 1/1.6/14.4/15. The results are shown in table 1.

EXAMPLE 3

A mixed metal oxide with a nominal composition of $Mo_1V_{0.3}Nb_{0.12}Sb_{0.09}Te_{0.09}O_x$ was prepared as follows:

Solution A: Ammonium vanadate (7.95 g) was dissolved in 165 mL water at 90° C. The solution was purged with nitrogen. Antimony (III) oxide (4.92 g) was added and the mixture was heated at 92° C. for about 4 hrs. Heating was discontinued and the mixture was cooled under nitrogen overnight.

Solution B: Ammonium para molybdate (40.0 g) was dissolved in 100 mL of water with heating. Telluric acid (4.7 g) was added to solution B and was dissolved. Solution B was cooled to room temperature.

Solution C: Oxalic acid dihydrate (20.6 g) was dissolved in warm water (165 mL). Niobic acid (4.7 g) was added and the mixture was heated to 95° C.–100° C. for one hour to give a clear. Solution C was cooled to room temperature.

Solution B was added to solution A followed by solution C. The resulting mixture was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground, pressed and sieved to 18/35 mesh. 2.7 g of this catalyst was tested for propane oxidation with a feed having a propane/O2/N2/water ratio of 1/3.0/27/14. The results are shown in table 1.

EXAMPLE 4

2.7 g of the catalyst prepared in example 3 was tested for propane oxidation with a feed having a propane/O2/N2/water ratio of 1/3.0/27/14. The results are shown in table 1.

EXAMPLE 5

1 g of the catalyst prepared in example 3 was tested for propane oxidation with a feed having a propane/O2/N2/water ratio of 1/3.0/27/14. The results are shown in table 1.

EXAMPLE 6

2.7 g of the catalyst prepared in example 3 was tested for propane oxidation with a feed having a propane/O2/N2/water ratio of 1/1.6/14.4/15. The results are shown in table 1.

COMPARATIVE EXAMPLE 1

A mixed metal oxide with a nominal composition of $Mo_1V_{0.3}Nb_{0.12}Te_{0.09}O_x$, was prepared as follows:

Solution A: Ammonium para molybdate (40.1 g) was dissolved in water (400 mL) with slight heating (70° C.). Ammonium vanadate (7.97 g) was added next and was dissolved. Telluric acid dihydrate (4.7 g) was dissolved next. The mixture was cooled to room temperature.

Solution B: Oxalic acid dihydrate (20.6 g) was dissolved in warm water (165 mL). Niobic acid (4.7 g) was added and the mixture was heated to 95° C. for one hour to give a clear solution. This solution was cooled to room temperature. Solution B was added to Solution A. The mixture was stirred overnight the spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground, pressed and sieved to 18/35 mesh. 1 g of this catalyst was tested for propane oxidation with a feed having a propane/O2/N2/water ratio of 1/3.0/27/14. The results are shown in table 1.

COMPARATIVE EXAMPLE 2

1 g of the catalyst prepared in comparative example 1 was tested for propane oxidation with a feed having a propane/O2/N2/water ratio of 1/3.0/27/14. The results are shown in table 1.

COMPARATIVE EXAMPLE 3

1 g of the catalyst prepared in comparative example 1 was tested for propane oxidation with a feed having a propane/O2/N2/water ratio of 1/1.6/14.4/15. The results are shown in table 1.

COMPARATIVE EXAMPLE 4

A mixed metal oxide with a nominal composition of $Mo_1V_{0.3}Nb_{0.05}Te_{0.09}O_x$ was prepared as follows:

Solution A: Ammonium para molybdate (40.1 g) was dissolved in water (400 mL) with slight heating (70° C.). Ammonium vanadate (7.97 g) was added next and was dissolved. Telluric acid dihydrate (4.7 g) was dissolved next. The mixture was cooled to room temperature.

Solution B: Oxalic acid dihydrate (8.6 g) was dissolved in warm water (100 mL). Niobic acid (1.9 g) was added and the mixture was heated to 95° C. for one hour to give a clear solution. This solution was cooled to room temperature. Solution B was added to Solution A. The mixture was stirred overnight the spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground, pressed and sieved to 18/35 mesh. 2 g of this catalyst was tested for propane oxidation with a feed having a propane/O2/N2/water ratio of 1/3.0/27/14. The results are shown in table 1.

COMPARATIVE EXAMPLE 5

2 g of the catalyst prepared in comparative example 1 was tested for propane oxidation with a feed having a propane/O2/N2/water ratio of 1/3.0/27/14. The results are shown in table 1.

COMPARATIVE EXAMPLE 6

2 g of the catalyst prepared in comparative example 1 was tested for propane oxidation with a feed having a propane/O2/N2/water ratio of 1/1.6/14.4/15. The results are shown in table 1.

COMPARATIVE EXAMPLE 7

A mixed metal oxide with a nominal composition of $Mo_1V_{0.3}Nb_{0.05}Sb_{0.15}O_x$ was prepared as follows:

Solution A: Ammonium vanadate (7.95 g) was dissolved in 165 mL water at 90° C. Antimony (III) oxide (4.92 g) was added and the mixture was purged with nitrogen and heated at 92° C. for about 4.5 hrs. Heating was discontinued and the mixture was cooled overnight under nitrogen. Water (105 mL) was removed by rotary evaporation. Ammonium par-amolybdate (40.0 g) was added and the mixture was stirred under nitrogen for 4.5 hrs.

Solution B: Niobium oxalate mono oxalate (7.12 g) was stirred in 40 mL water for 5 hrs. Solution B was added to solution A and the resulting mixture was spray dried to give a solid catalyst precursor. The catalyst precursor was heated in air at 120° C. for 1 hr, then decomposed at 300° C. for 5 hrs, then calcined in argon at 600° C. for 2 hrs. The resulting powder was ground, pressed and sieved to 18/35 mesh. 1 g of this catalyst was tested for propane oxidation with a feed having a propane/O2/N2/water ratio of 1/1.6/14.4/15. The results are shown in table 1.

COMPARATIVE EXAMPLE 8

1 g of the mixed metal oxide prepared in comparative example 7 was tested for propane oxidation with a feed having a propane/O2/N2/water ratio of 1/1.6/14.4/15. The results are shown in table 1.

COMPARATIVE EXAMPLE 9

1 g of the mixed metal oxide prepared in comparative example 7 was tested for propane oxidation with a feed having a propane/O2/N2/water ratio of 1/1.6/14.4/15. The results are shown in table 1.

COMPARATIVE EXAMPLE 10

A mixed metal oxide with a nominal composition of $Mo_1V_{0.5}Te_{0.5}O_x$ was prepared as follows:

Solution A: Ammonium para molybdate (20.1 g) was dissolved in water (200 mL) with slight heating (70° C.). Ammonium vanadate (36.6 g) was added next and was dissolved. Telluric acid dihydrate (13.0 g) was dissolved next. The mixture was cooled to room temperature and stirred overnight. Water was removed by rotevap at 50° C. The paste was dried in an oven at 50° C. for several days. The catalyst precursor was heated in air at 120° C. for 1 hr, then decomposed at 300° C. for 5 hrs, then calcined in argon at 600° C. for 2 hrs. The resulting powder was ground, pressed and sieved to 18/35 mesh. 4.6 g of this catalyst was tested for propane oxidation with a feed having a propane/O2/N2/water ratio of 1/3.0/27/14. The results are shown in table 1.

For each of the catalysts from the Examples above, a specified amount of catalyst mixed with quartz chips to make a 5 cc catalyst bed which was placed into a downflow packed bed reactor. The reactor was heated to a temperature as specified in Tables 1. A mixture of propane, oxygen, nitrogen and steam was supplied to the reactor at a percent by volume and a rate as specified in each example. The reaction continued at the pressure specified in Table 1 and for at least three hours. The %conversion and the %selectivity were calculated and are reported in Table 1.

TABLE 1

| Examples | Catalyst Bed TEMP (° C.) | RX Inlet Pressure Psig | Reactant's Residence Time (sec) | GHSV L gas/L cat-hr. | Wt % Propane Conversion | AA Selectivity | AA YIELD |
|---|---|---|---|---|---|---|---|
| Ex. 1 | 400 | 32 | 1.63 | 2856 | 59 | 50.0 | 29.5 |
| Ex. 2 | 400 | 20 | 1.00 | 3458 | 52 | 56.3 | 29.2 |
| Ex. 3 | 410 | 32 | 1.28 | 3561 | 80 | 52.1 | 41.5 |
| Ex. 4 | 380 | 32 | 1.01 | 4729 | 48 | 62.6 | 30.0 |
| Ex. 5 | 400 | 20 | 0.27 | 12620 | 33 | 66.7 | 22.3 |
| Ex. 6 | 400 | 20 | 0.71 | 4872 | 48 | 65.3 | 31.1 |
| Comp. Ex. 1 | 380 | 32 | 0.37 | 12942 | 60 | 42.9 | 25.9 |
| Comp. Ex. 2 | 400 | 20 | 0.27 | 12817 | 64 | 39.5 | 25.5 |
| Comp. Ex. 3 | 400 | 20 | 0.26 | 13045 | 59 | 50.7 | 30.0 |
| Comp. Ex. 4 | 360 | 20 | 0.57 | 6466 | 82 | 46.2 | 37.9 |
| Comp. Ex. 5 | 350 | 32 | 0.78 | 6457 | 82 | 43.8 | 35.7 |
| Comp. Ex. 6 | 360 | 20 | 0.41 | 8998 | 61 | 52.3 | 31.9 |

TABLE 1-continued

| Examples | Catalyst Bed TEMP (° C.) | RX Inlet Pressure Psig | Reactant's Residence Time (sec) | GHSV L gas/L cat-hr. | Wt % Propane Conversion | AA Selectivity | AA YIELD |
|---|---|---|---|---|---|---|---|
| Comp. Ex. 7 | 400 | 20 | 0.36 | 9703 | 40 | 40.0 | 16.2 |
| Comp. Ex. 8 | 400 | 20 | 0.22 | 15363 | 30 | 45.7 | 13.8 |
| Comp. Ex. 9 | 400 | 20 | 0.27 | 12785 | 33 | 41.4 | 13.8 |
| Comp. Ex. 10 | 410 | 32 | 2.84 | 1608 | 4 | 44.4 | 1.9 |

The Examples above demonstrate the benefits of the presence of tellurium and antimony in a mixed metal oxide molybdovanate catalyst in the conversion of an alkane to an unsaturated carboxylic acid in a one-step process. As shown by a comparison of Example 5 with Comparative Example 2 and Comparative Example 9, the presence of both tellurium and antimony in a molydovanadate catalyst (Example 5) results in better selectivity to acrylic acid than for a molydovanadate catalyst with tellurium without antimony (Comparative Example 2) or with antimony without tellurium (Comparative Example 9).

Obviously, numerous modifications and variations of the present invention are possible in light of the above teachings. It is therefore to be understood that within the scope of the appended claims, the invention may be practiced otherwise than as specifically described herein.

The catalyst of the present invention can be rejuvenated by adding the same compounds which may be used in the synthesis of the catalyst, e.g., molybdenum salts, such as ammonium paramolybdate, molybdenum oxides, molybdic acids or molybdenum chlorides; vanadium salts, such as ammonium metavanadate, vanadium oxides or vanadium sulfates; niobium oxalate, ammonium niobium oxalate, niobium oxide hydrous niobium oxide or niobic acid; oxides of metals, such as silver, silicon, sulfur, zirconium, titanium, aluminum, copper, lithium, sodium, potassium, rubidium, cesium, gallium, iron, rhenium, cobalt, chromium, manganese, indium, thallium, bismuth, germanium, tin, cerium or lanthanum; ammonium hydrogen phosphate, ammonium phosphate, phosphorus pentoxide, phosphoric acid, phosphorus acid, arsenic acid and arsenic oxide. If water-soluble, the desired compound can be added with water into the vessel containing the catalyst.

The catalyst and process of the present invention are applicable to different reaction systems, such as fixed bed, moving bed and fluidized bed reactors. The catalyst particle size and process conditions can be altered for the desired reaction system.

What is claimed is:

1. A process for producing an unsaturated carboxylic acid from an alkane comprising:
    contacting an alkane and molecular oxygen with a catalyst composition of the formula:

$MoV_aNb_bTe_cSb_dM_eO_x$ wherein Mo is molybdenum, V is vanadium, Nb is niobium, Te is tellurium, Sb is antimony and M is one or more elements selected from the group consisting of silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium and lanthanum; a is 0.05 to 0.99; b is 0.01 to 0.99; c is 0.01 to 0.15; d is 0.01 to 0.2; e is 0 to 0.5; and x is determined by the valence requirements of the other components of the catalyst composition.

2. The process of claim 1 wherein a is 0.1 to 0.5.
3. The process of claim 2 wherein a is 0.3.
4. The process of claim 1 wherein b is 0.05 to 0.2.
5. The process of claim 4 wherein b is 0.05 to 0.12.
6. The process of claim 1 wherein c is 0.01 to 0.12.
7. The process of claim 6 wherein c is 0.01 to 0.10.
8. The process of claim 1 wherein d is 0.01 to 0.15.
9. The process of claim 8 wherein d is 0.03 to 0.1.
10. The process of claim 1 wherein e is 0.01 to 0.25.
11. The process of claim 10 wherein e is 0.02 to 0.1.
12. The process of claim 1 wherein the catalyst is a supported catalyst on an inert support.
13. The process of claim 12 wherein the inert support is silica, alumina, niobia, titania, zirconia or mixtures thereof.
14. The process of claim 13 wherein the catalyst composition is in the form of powder, granules, spheres, cylinders or saddles.
15. The process of claim 1 wherein the catalyst is selected from the group consisting of $MoV_{0.3}Nb_{0.05}Te_{0.06}Sb_{0.15}O_x$ and $MoV_{0.3}Nb_{0.12}Te_{0.09}Sb_{0.09}O_x$.
16. A process for producing acrylic acid from propane comprising:
    contacting propane and molecular oxygen with a catalyst composition of the formula:

$MoV_aNb_bTe_cSb_dM_eO_x$ wherein Mo is molybdenum, V is vanadium, Nb is niobium, Te is tellurium, Sb is antimony and M is one or more elements selected from the group consisting of silver, silicon, sulfur, zirconium, titanium, aluminum, copper, lithium, sodium, potassium, rubidium, cesium, gallium, phosphorus, iron, rhenium, cobalt, chromium, manganese, arsenic, indium, thallium, bismuth, germanium, tin, cerium and lanthanum; a is 0.05 to 0.99; b is 0.01 to 0.99; c is 0.01 to 0.15; d is 0.01 to 0.2; e is 0 to 0.5; and x is determined by the valence requirements of the other components of the catalyst composition.

17. The process of claim 16 wherein a is 0.1 to 0.5.
18. The process of claim 17 wherein a is 0.3.
19. The process of claim 16 wherein b is 0.05 to 0.2.
20. The process of claim 19 wherein b is 0.05 to 0.12.
21. The process of claim 16 wherein c is 0.01 to 0.12.
22. The process of claim 21 wherein c is 0.01 to 0.10.
23. The process of claim 16 wherein d is 0.01 to 0.15.
24. The process of claim 23 wherein d is 0.03 to 0.1.
25. The process of claim 16 wherein e is 0.01 to 0.25.
26. The process of claim 25 wherein e is 0.02 to 0.1.
27. The process of claim 16 wherein the catalyst is selected from the group consisting of $MoV_{0.3}Nb_{0.05}Te_{0.06}Sb_{0.15}O_x$ and $MoV_{0.3}Nb_{0.12}Te_{0.09}Sb_{0.09}O_x$.
28. The process of claim 16 in which the propane:oxygen molar ratio is in the range from 1:1 to 2:1.

* * * * *